(12) United States Patent
Kyung

(10) Patent No.: US 6,296,481 B1
(45) Date of Patent: Oct. 2, 2001

(54) INDIRECT BONDING BRACKET POSITIONER FOR CORRECTION OF IRREGULARITIES OF THE TEETH

(76) Inventor: Hee M. Kyung, Ulzi Apt. 101-803, 314-2 Beomeo 4 Dong, Susung Gu Taegu (KR)

( * ) Notice: Subject to any disclaimer, the term of this patent is extended or adjusted under 35 U.S.C. 154(b) by 0 days.

(21) Appl. No.: 09/712,434

(22) Filed: Nov. 14, 2000

(30) Foreign Application Priority Data

Dec. 31, 1999 (KR) .................................................. 99-30664

(51) Int. Cl.[7] .................................................... A61C 3/00
(52) U.S. Cl. .................................................. 433/3; 433/24
(58) Field of Search ..................... 433/3, 24, 74

(56) References Cited

U.S. PATENT DOCUMENTS

| | | | | |
|---|---|---|---|---|
| 1,082,052 | * | 12/1913 | Strang | 433/20 |
| 3,439,421 | * | 4/1969 | Perkowski | 433/24 |
| 3,949,478 | * | 4/1976 | Schinhammer | 433/3 |
| 4,183,141 | * | 1/1980 | Dellinger et al. | 433/3 |
| 4,431,409 | * | 2/1984 | Picard | 433/2 |
| 5,055,038 | * | 10/1991 | Ronay et al. | 433/24 |
| 5,100,316 | * | 3/1992 | Wildman | 433/24 |

FOREIGN PATENT DOCUMENTS 10-0247408 * 5/1999 (KR) .

* cited by examiner

Primary Examiner—John J. Wilson
(74) Attorney, Agent, or Firm—John K. Park; Park & Sutton LLP

(57) ABSTRACT

An orthodontic bracket positioner includes a metal plate placed under a tongue, a pair of side elongated slots formed along a side edge portion of the metal plate, a circular hole formed in a front edge portion of the metal plate and adjacent to the side elongated slots. A pair of side bracket holders substantially elongated to sufficiently hold brackets for a canine tooth and molar teeth behind the canine tooth, a front edge line of a front bracket holder arc-shaped in a similar manner to the front teeth line to fixedly hold four front teeth at the same time. The side elongated slots of the metal plate are perpendicular to an open type connection slot formed at a portion of each of the bracket holders, the bracket holders including a plurality of fixing slots formed along an edge line thereof so as to engage a plurality of brackets therethrough.

13 Claims, 4 Drawing Sheets

INDIRECT BONDING BRACKET POSITIONER FOR CORRECTION OF IRREGULARITIES OF THE TEETH

CLAIMING FOREIGN PRIORITY

The applicant claims and requests a foreign priority, through the Paris Convention for the Protection of Industry Property, based on a patent application filed in the Republic of Korea (South Korea) with the filing date of Dec. 31, 1999, with the application number 1999-30664, by the applicant. (See the Attached Declaration)

BACKGROUND OF THE INVENTION

The present invention relates to an orthodontic bracket positioner applicable to a teeth arrangement using inner sides of the teeth for bracket attachment.

In general, an orthodontic therapy for teeth arrangement includes a direct bracket bonding method and an indirect bracket bonding method. For the direct bonding, a plurality of brackets are bonded on target teeth sides within an orthodontic patient's oral cavity. For the conventional indirect bonding, the orthodontic brackets are initially attached to a plaster model with eye-watching to realize a more precise bracket position and then transferred into the oral cavity to bond the brackets onto target teeth sides. However, it is not easy to get an accurate bracket position even on the plaster model especially in lingual sides without using any kind of instrument.

So to improve the accuracy of the lingual bracket position, Korea Patent Application No. 1998-008587 by the present inventor has disclosed an improvement of an orthodontic bracket positioner for inner teeth side application, wherein an elongated slot is formed along an edge portion of a horizontal metal plate. A plurality of bracket holders are engaged to the elongated slot by a bolt and nut with a spring so that the bracket holders are movable along the slot. However, such a conventional device has a disadvantage in that the brackets are not easily released from the bracket holder. To release the bolt and nut, connecting mechanism, from the fixedly engaged position, the bolt and nut has to be unfastened each time when the bracket holder needs to be removed from the metal plate.

There is a significant effort by the dental physician and discomfort to the patient each time the bracket holder needs to be removed or repositioned from the metal plate. This disadvantage highlights the need for an orthodontic design.

SUMMARY OF THE INVENTION

The present invention is contrived to overcome the conventional disadvantages and others. Accordingly, it is an object of the present invention to provide an orthodontic bracket positioner applicable to a teeth arrangement using inner sides of teeth for bracket bonding which enables bracket holder detachment from a metal plate without releasing a bolt or nut. Simply loosening of the bolt and nut allows the bracket holder to be repositioned.

To achieve the above-described object, the orthodontic bracket positioner according to the present invention comprises a metal plate placed under a tongue, a pair of side elongated slots formed along a side edge portion of the metal plate, a circular hole formed in a front edge portion of the metal plate and adjacent to the side elongated slots. A pair of side bracket holders substantially elongated to sufficiently hold brackets for a canine tooth and molar teeth behind the canine tooth, a front edge line of a front bracket holder arc-shaped in a similar manner to the front teeth line to fixedly hold four front teeth at the same time. The side elongated slots of the metal plate are perpendicular to an open type connection slot formed at a portion of each of the bracket holders, the bracket holders including a plurality of fixing slots formed along an edge line thereof so as to engage a plurality of brackets therethrough. A front bracket holder connected to the metal plate by a circular hole formed in a front edge portion of the metal plate, wherein the front bracket holder includes an arc-shaped fixing slot formed along an outer edge thereof, wherein a plurality of brackets are connected through the arc-shaped fixing slop; and wherein a bolt and a nut with a spring are employed to connect the side and front bracket holders through the side elongated slots and the circular hole to the metal plate.

In further explanation and detail an orthodontic bracket positioner comprises a plate having a pair of side elongated slots and a side edge portion. The pair of side elongated slots are formed along the side edge portion of the plate. A pair of side bracket holders, each having an open type connection slot, a side edge line, and a fixing slot along the side edge line. A plurality of orthodontic brackets and a connecting mechanism. The connecting mechanism is employed to connect the open type connection slot of the pair of side bracket holders through the side elongated slots to the plate. The connecting mechanism can be loosened to allow removal or repositioning of the side bracket holders, without completely detaching the connecting mechanism.

The side elongated slots of the plate are substantially perpendicular to the open type connection slots formed at a portion of each of the side bracket holders. The side bracket holders each include the fixing slots formed along the side edge line thereof so as to removably attach the orthodontic bracket therethrough.

The plate further having a front edge portion, with the front edge portion having a front hole. A front bracket holder, having an open type connection slot, an outer edge line, and a front fixing slot. The front hole is adjacent to the side elongated slots and the connecting mechanism is employed through the front hole and the open type connection slot to connect the front bracket holder to the plate. The connecting mechanism can be loosened to allow removal or repositioning of the front bracket holder, without completely detaching the connecting mechanism. The front bracket holder includes the front fixing slot formed along the outer edge line, so as to removably attached the orthodontic bracket therethrough.

The outer edge line of the front bracket holder can be arc-shaped. The front fixing slot of the front bracket holder is arc-shaped. The plate further includes a fixture aperture. The plate has a front aperture, a front edge line and a separate bracket holder, having an open type connection slot and a bracket hole. The front aperture is located near the front portion of the plate and the front aperture and the open type connection slot receive the connecting mechanism thus connecting the plate to the separate bracket holder. The bracket is attached to the separate bracket holder at the bracket hole, wherein the side bracket holders and orthodontic bracket are fixedly supported against the side teeth, such that pressure is applied to the front teeth by the separate bracket holder. The front aperture is an elongated arc shape and the front edge line of the metal plate is formed in an arc.

Although the present invention is briefly summarized, the fuller understanding of the invention can be obtained by the following drawings, detailed description and appended claims.

BRIEF DESCRIPTION OF DRAWINGS

These and other features, aspects and advantages of the present invention will become better understood with reference to the accompanying drawings, wherein.

DETAILED DESCRIPTION OF THE PREFERRED EMBODIMENTS

With reference to the accompanying drawings, the preferred embodiment of the orthodontic bracket positioner 50, used under a tongue or the top of the mouth, will now be described.

Figure 1:
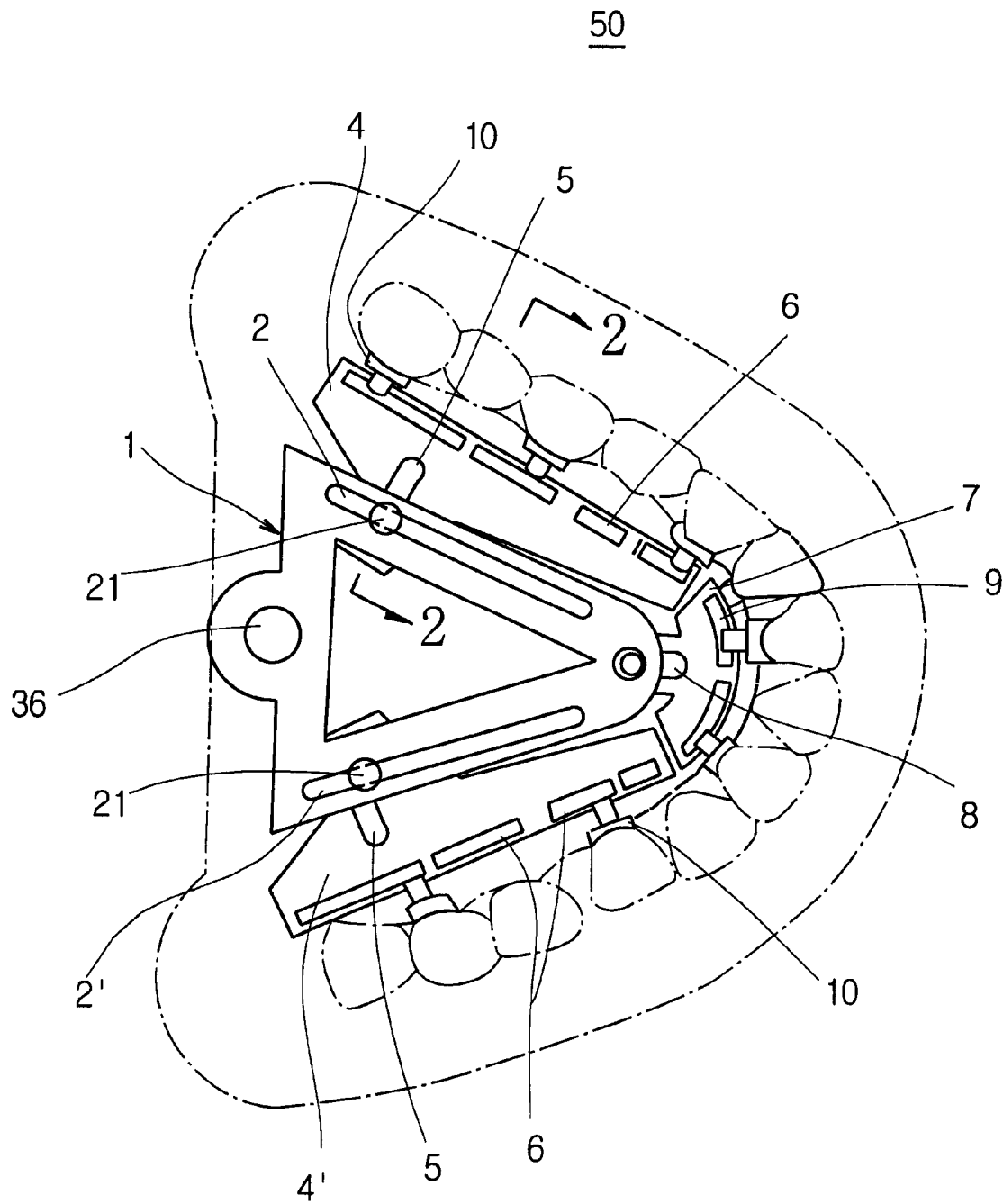
FIG. 1 is a plan view illustrating an orthodontic racket positioner according to an embodiment of the present invention.
Figure 2:
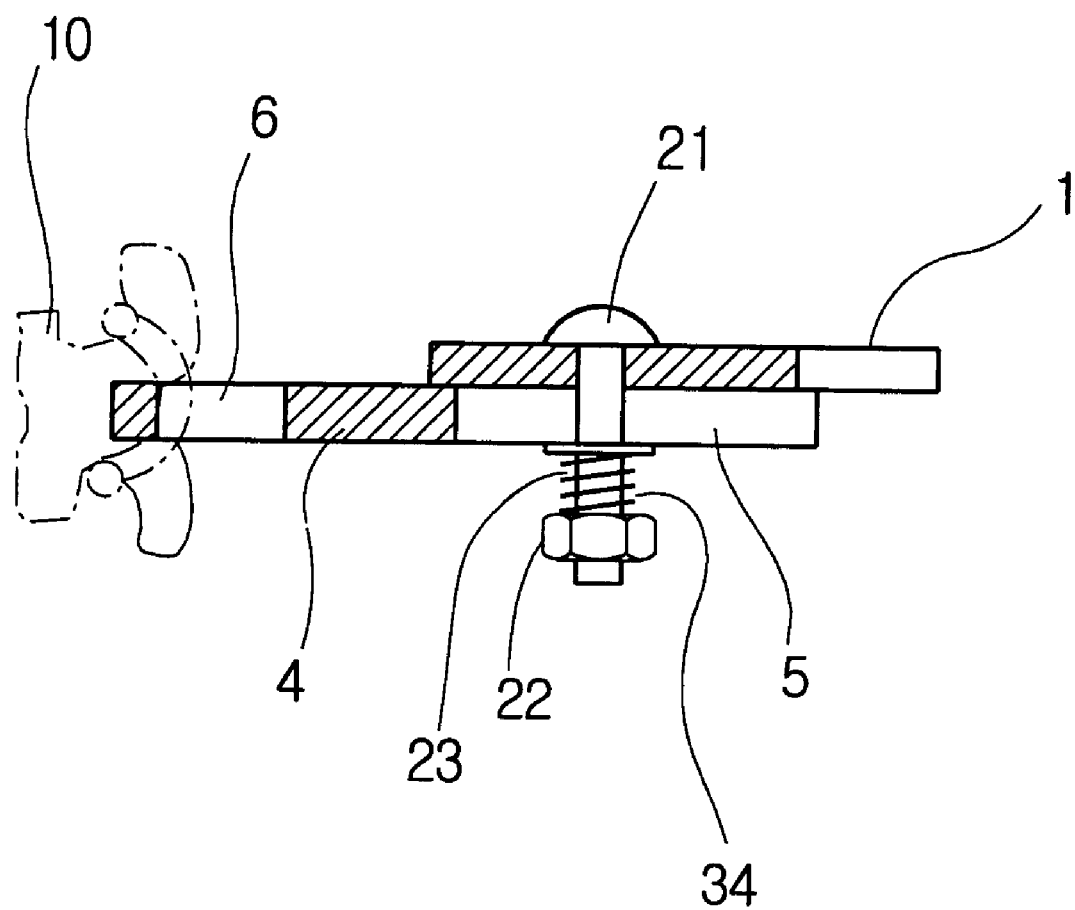
FIG. 2 is a cross-sectional view taken along line 2—2 in FIG. 1.
Figure 3:
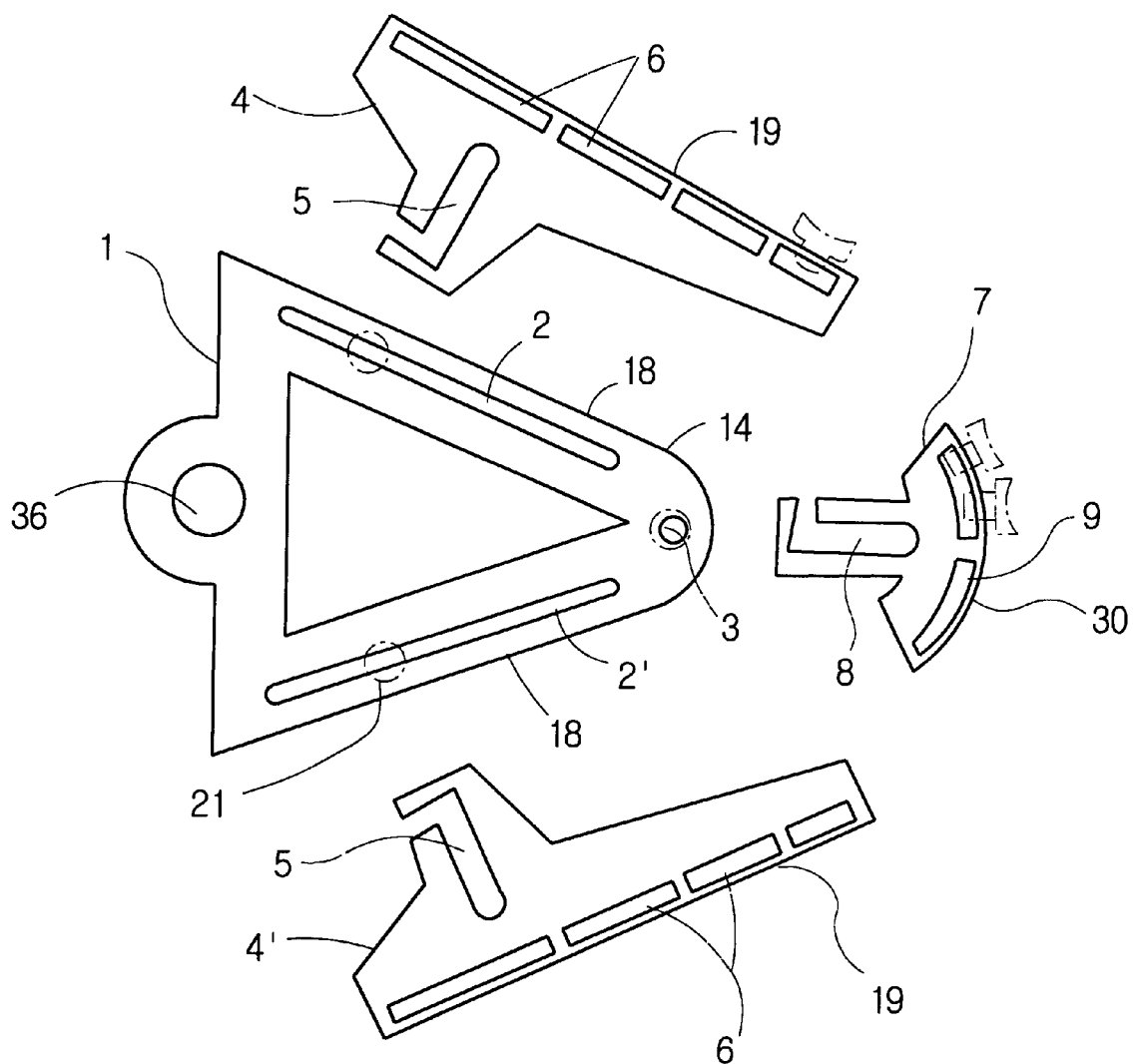
FIG. 3 is an exploded view of the orthodontic bracket positioner according to the present invention.

As shown in FIGS. 1–3, in a first embodiment, along side edge portion 18 of a plate 1 are formed a pair of side elongated slots 2, 2'. A circular hole 3 is formed through a front edge portion 14 of the plate 1. Plate 1 can be formed of metal, plastic, resin or other materials. The hole 3 can take other shapes including an elongated arc shaped hole 3 or in one version a front aperture 32 is located at the front edge portion 14.

Side bracket holders 4, 4' for side teeth are substantially elongated so as to sufficiently bond orthodontic bracket 10 onto a canine teeth and all the molar teeth at the same time. The bracket holders 4, 4' respectively include an open type connection slot 5 formed perpendicular to the elongated slots 2, 2' so that the bracket holders 4, 4' can be removably attached to the metal plate 1. A plurality of fixing slots 6 for orthodontic bracket 10 insertion therethrough are formed along side edge line 19 of the bracket holders 4, 4' so that brackets 10 can be easily and securely fastened to the bracket holders 4, 4'.

A front bracket holder 7 for incisors which is engaged to the metal plate 1 using the circular hole 3 also includes an open type connection slot 8, in a similar manner to the connection slot 5 of the bracket holder 4, 4'. At least one fixing slot 9 through which orthodontic brackets 10 are attached is formed in an arc shape similar to that of front teeth line, thereby enabling the front bracket holder 7 to be removably attached to the metal plate 1 with ease. The hole 3 or the fixing slot 9 can be circular or can take other elongated shapes. The outer edge line 30 of the front bracket holder 7 can be arc-shaped, in a similar manner to the front teeth line to fixedly hold all four front Incisor teeth at the same time.

Figure 4:
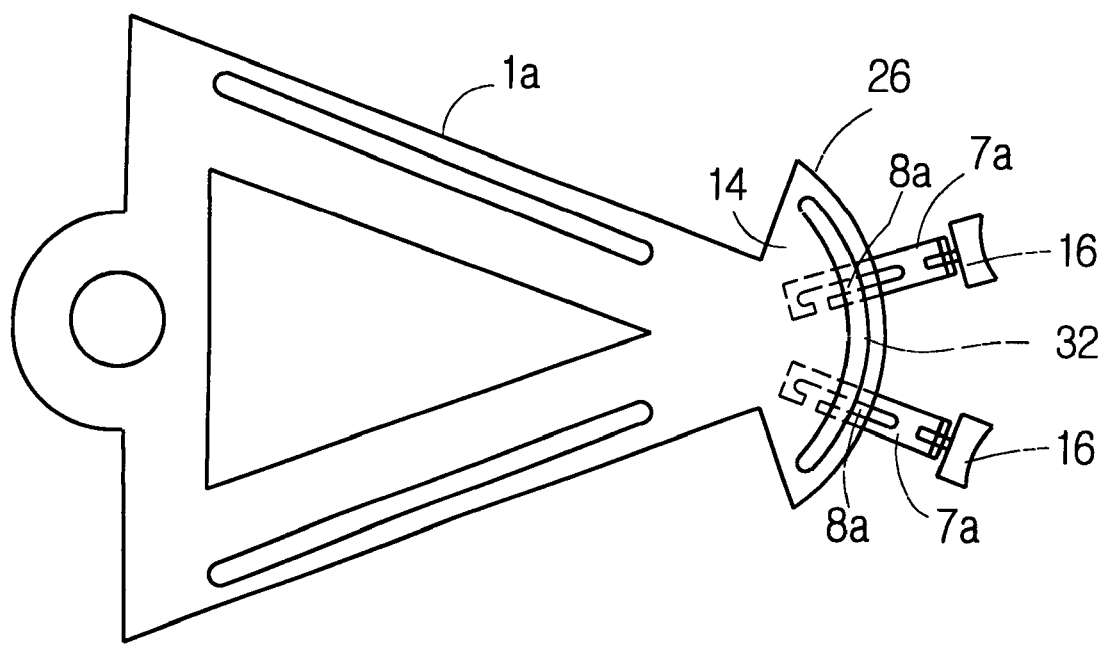
FIG. 4 is a plan view illustrating an orthodontic bracket positioner according to another embodiment of the present invention.

As further shown in FIG. 4, a metal plate 1a according to a second embodiment includes a front aperture 32. The front aperture 32 can be an arc-elongated slot in a similar manner to the front teeth line so that a plurality of separate bracket holders 7a each holding one orthodontic bracket 10 can be detachably attached to the metal plate 1a. Specifically, the front portion 14 of the metal plate 1a is formed in an arc shape and the elongated front aperture 32 is also shaped in an arc along the arc shaped front portion 14 of the metal plate 1a. Each of the separate bracket holders 7a includes a circular bracket hole 16 so that a orthodontic bracket 10 can be fixed to the separate bracket holder 7a using a connection wire through the circular bracket hole 16. Alternately, the bracket holder 7 according to the first embodiment can be also attached to the metal plate 1a using the front aperture 32.

As shown back in FIGS. 1–3, the side bracket holders 4, 4' and front bracket holder 7 are connected to the metal plate 1 using the side elongated slots 2, 2' and the front aperture 32 or circular hole 3, and a connecting mechanism 34. The connecting mechanism 34 can include a bolt 21 and nut 22 employed with insertion of the spring 23. The connecting mechanism 34 is inserted through the open type connection slots 5 to connect the pair of side bracket holders 4,4' through the side elongated slots 2,2' to the plate 1 whereby the connecting mechanism 34 can be loosened to allow removal or repositioning of the side bracket holders 4, 4', without completely detaching the connecting mechanism 34.

FIG. 2, in particular shows, the connection of the pair of side bracket holders 4,4' through the side elongated slots 2,2' to the plate 1. FIG. 2 is a view taken along a cut line 2—2 from FIG. 1. The connecting mechanism 34 is shown as bolt 21 and nut 22 employed with insertion of the spring 23. The spring 23 provides pressure to so that the interface between side bracket holders 4,4' and the plate 1 is tight and secure with minimal gap.

The use of open type connection slots 5 with connecting mechanism 34 fulfills a significant advantage and objective of the invention, which is eliminating the necessity to completely remove connecting mechanism 34 from the plate 1, in order to remove or reposition the side bracket holders 4, 4'. After the connecting mechanism 34 is loosened, the open type connection slot 5 having one side open is simply slid away from the connecting mechanism 34 through the open side.

Reattaching the side bracket holders 4, 4' occurs in reverse manner. The open type connection slot 5 is simply slid around the connecting mechanism 34 through the open side, then the connecting mechanism 34 is tightened to fixedly attach the side bracket holders 4, 4' to the plate 1. Front bracket holder 7 is connected in a similar manner by the connecting mechanism 34 through the open type connection slot 8 with hole 3. In FIG. 4 separate bracket holder 7a is connected in a similar manner by the connecting mechanism 34 through the open type connection slot 8a with the front aperture 32.

Consequently, the bracket holders 4, 4' are connected to the metal plate 1 using the bolt 21, nut 22 and spring 23 applied to the elongated slots 2, 2', and the orthodontic brackets 10 are attached to the bracket holders 4, 4'. Then the orthodontic brackets 10 are placed next to or bonded onto the target teeth sides at the same time. In order to complete the connection between the bracket holders 4, 4' and the metal plate 1, a portion near the open type connection slot 5 is simply hooked on the bolt 21. The bolt 21 and nut 22 are tightened to securely attach the bracket holders 4, 4' to the metal plate 1. The detachment of the bracket holders 4, 4' from the metal plate 1 can be easily performed using the reverse order of the connection.

Front bracket holder 7 is connected to the metal plate 1 in a similar manner as side bracket holders 4 and 4', using the circular hole 3. Additional bolt 21, nut 22 and spring 23 are used for attaching bracket holder 7.

Prior to insertion of the orthodontic bracket positioner 50 into the mouth the orthodontic brackets 10 can be properly aligned to apply appropriate pressure upon the teeth. A positioning device, not shown, can be used to securely hold the orthodontic bracket positioner 50 adjacent to a molded impression of the patients teeth. A fixture aperture 36 can be included on the plate 1, which allows the plate 1 to be securely positioned and held by the positioning device.

In FIG. 4, each of the separate bracket holders 7a is similar in construction and operation to that of the first embodiment having a open type connection slot 8a, and its front portion is similar to the previously described Korea Patent Application No. 1998-008587 by the same inventor. However, a bracket holder for holding a single orthodontic bracket is also detachably attached to the metal plate 1a by the use of the open type connection slot 8a.

As discussed above, the orthodontic bracket positioner according to the prevent invention provides the side teeth bracket holders 4, 4' which can be easily connected to the metal plate 1, wherein the brackets 10 are attached to the bracket holders 4, 4', thereby enabling the bracket bonding operation to be faster with greater convenience.

Although the invention has been described in considerable detail with reference to certain preferred versions thereof, other versions are possible by converting the aforementioned construction. Therefore, the scope of the invention shall not be limited by the specification detailed above and the appended claims.

What is claimed is:

1. An orthodontic bracket positioner, comprising:
   a) a plate having a pair of side elongated slots, a side edge portion, wherein the pair of side elongated slots are formed along the side edge portion of the plate;
   b) a pair of side bracket holders, each having an open type connection slot, a side edge line, and a fixing slot along the side edge line;
   c) a plurality of orthodontic brackets; and
   d) a connecting mechanism, wherein the connecting mechanism is employed to connect the open type connection slot of the pair of side bracket holders through the side elongated slots to the plate, whereby the connecting mechanism can be loosened to allow removal or repositioning of the side bracket holders, without completely detaching the connecting mechanism;
   wherein the side elongated slots of the plate are substantially perpendicular to the open type connection slots formed at a portion of each of the side bracket holders, wherein the side bracket holders each include the fixing slot formed along the side edge line thereof so as to removably attach the orthodontic bracket therethrough.

2. The orthodontic bracket positioner of claim 1 further comprising:
   a) the plate further having a front edge portion, the front edge portion having a front hole; and
   b) a front bracket holder, having an open type connection slot, an outer edge line, and a front fixing slot;
   wherein the front hole is adjacent to the side elongated slots, wherein the connecting mechanism is employed through the front hole and the open type connection slot to connect the front bracket holder to the plate; whereby the connecting mechanism can be loosened to allow removal or repositioning of the front bracket holder, without completely detaching the connecting mechanism;
   wherein the front bracket holder includes the front fixing slot formed along the outer edge line, so as to removably attached the orthodontic bracket therethrough.

3. The orthodontic bracket positioner of claim 2, wherein the outer edge line of the front bracket holder is arc-shaped.

4. The orthodontic bracket positioner of claim 3, wherein the front fixing slot of the front bracket holder is arc-shaped.

5. The orthodontic bracket positioner of claim 4, wherein the plate is a metal plate.

6. The orthodontic bracket positioner of claim 5, wherein the connecting mechanism is a bolt and a nut.

7. The orthodontic bracket positioner of claim 6, wherein the plate further includes a fixture aperture.

8. The orthodontic bracket positioner of claim 1 further comprising;
   a) the plate having a front aperture and a front edge line;
   b) a separate bracket holder, having an open type connection slot and a bracket hole;
   wherein the front aperture is located near the front portion of the plate and the front aperture and the open type connection slot receive the connecting mechanism thus connecting the plate to the separate bracket holder, wherein the bracket is attached to the separate bracket holder at the bracket hole, wherein the side bracket holders and orthodontic bracket are fixedly supported against the side teeth, such that pressure is applied to the front teeth by the separate bracket holder.

9. The orthodontic bracket positioner of claim 8, wherein the front aperture is an elongated arc shape.

10. The orthodontic bracket positioner of claim 9, wherein the front edge line of the plate is formed in an arc.

11. The orthodontic bracket positioner of claim 10, wherein the plate is a metal plate.

12. The orthodontic bracket positioner of claim 11, wherein the connecting mechanism is a bolt and a nut.

13. The orthodontic bracket positioner of claim 12, wherein the plate further includes a fixture aperture.

* * * * *